United States Patent

Sinnreich et al.

[11] Patent Number: 5,827,984
[45] Date of Patent: Oct. 27, 1998

[54] APPARATUS FOR SIMULATING THE EFFECT OF THE LIVING ORGANISM ON THE CHANGE IN SHAPE, THE DISINTEGRATION AND DISSOLUTION BEHAVIOUR AND THE ACTIVE-INGREDIENT RELEASE OF A PHARMACEUTICAL DOSAGE FORM

[75] Inventors: Joel Sinnreich, Basel; Christian Bosshard, Hersberg, both of Switzerland

[73] Assignee: Ciba Geigy Corporation, Summit, N.J.

[21] Appl. No.: 592,419

[22] PCT Filed: Jul. 28, 1994

[86] PCT No.: PCT/EP94/02485

§ 371 Date: Feb. 6, 1996

§ 102(e) Date: Feb. 6, 1996

[87] PCT Pub. No.: WO95/15329

PCT Pub. Date: Jun. 8, 1995

[30] Foreign Application Priority Data

Aug. 6, 1993 [CH] Switzerland ............... 2349/93

[51] Int. Cl.⁶ .................................................. G01N 33/15
[52] U.S. Cl. ...................... 73/866; 73/865.6; 366/142
[58] Field of Search ..................... 73/866, 865.6, 73/53.01; 366/142, 143

[56] References Cited

U.S. PATENT DOCUMENTS

| 2,530,065 | 11/1950 | King . | |
|---|---|---|---|
| 3,618,395 | 11/1971 | Melliger | 73/866 |
| 3,791,221 | 2/1974 | Kirschner et al. | 73/866 |
| 3,802,272 | 4/1974 | Bischoff . | |
| 4,855,821 | 8/1989 | Swon et al. | 73/866 |
| 4,964,310 | 10/1990 | Schneider | 73/866 |
| 5,412,979 | 5/1995 | Fassihi | 73/866 |

FOREIGN PATENT DOCUMENTS

| 2409222 | 4/1975 | Germany . |
|---|---|---|
| 2530065 | 3/1977 | Germany . |
| 3715961 | 11/1988 | Germany . |
| 2136123 | 9/1984 | United Kingdom . |

OTHER PUBLICATIONS

Aoki et al., International Journal of Pharmaceutics, vol. 95, pp. 67–75 (1993).
SOTAX DT3 tablet–disintegration testing apparatus brochure.
USP XXII, pp. 1577–1583 (1990).

Primary Examiner—Hezron E. Williams
Assistant Examiner—Nashmiya Ashraf
Attorney, Agent, or Firm—Marla J. Mathias

[57] ABSTRACT

An apparatus for simulating the effect of a living organism on the change in shape, the disintegration and dissolution behaviour and the active-ingredient release of a pharmaceutical dosage form, including a beaker-shaped container for accommodating a test medium and the pharmaceutical dosage form and an agitating device for agitating the test medium, which agitating device can be moved periodically in a reciprocating movement into and back out of the container, wherein the agitating device includes a piston-shaped head portion arranged on a piston rod, which head portion is provided with through-openings for the test medium and the distance of the piston-shaped head portion from the container floor can be altered periodically in accordance with the periodic reciprocating movement of the agitating device, wherein, the piston rod is suspended from a gallows-shaped boom or the piston rod passes through a bore in the gallows-shaped boom in such a manner that downward movement of the piston-shaped head portion arranged on the piston rod is caused by gravity alone and wherein there is arranged in the container an intermediate base supported on the container floor, the base being provided with through-openings for the test medium and serving as a support for the dosage form, wherein the distance between the intermediate base and the container floor is adjustable by a device for adjusting the distance between the base and the floor.

23 Claims, 3 Drawing Sheets

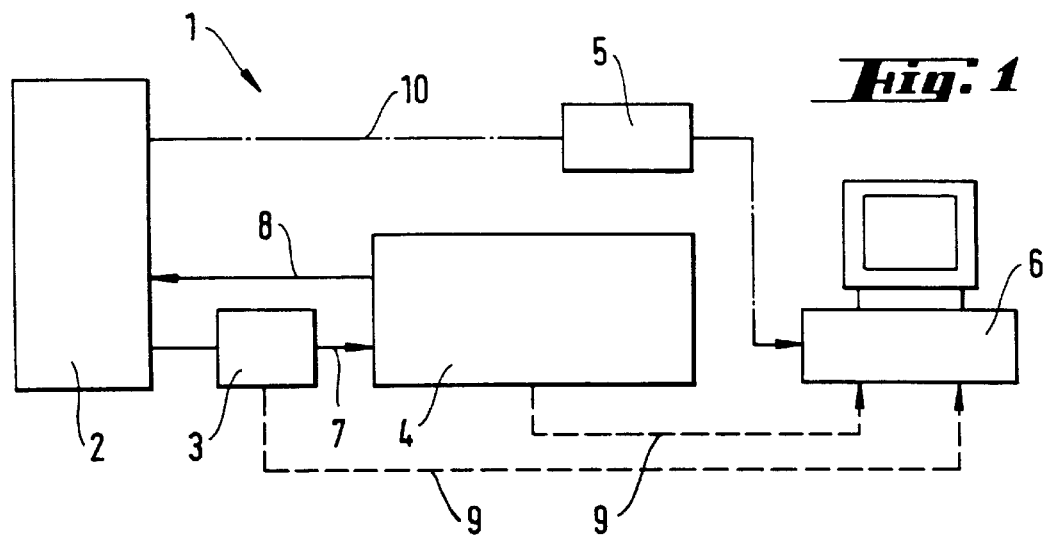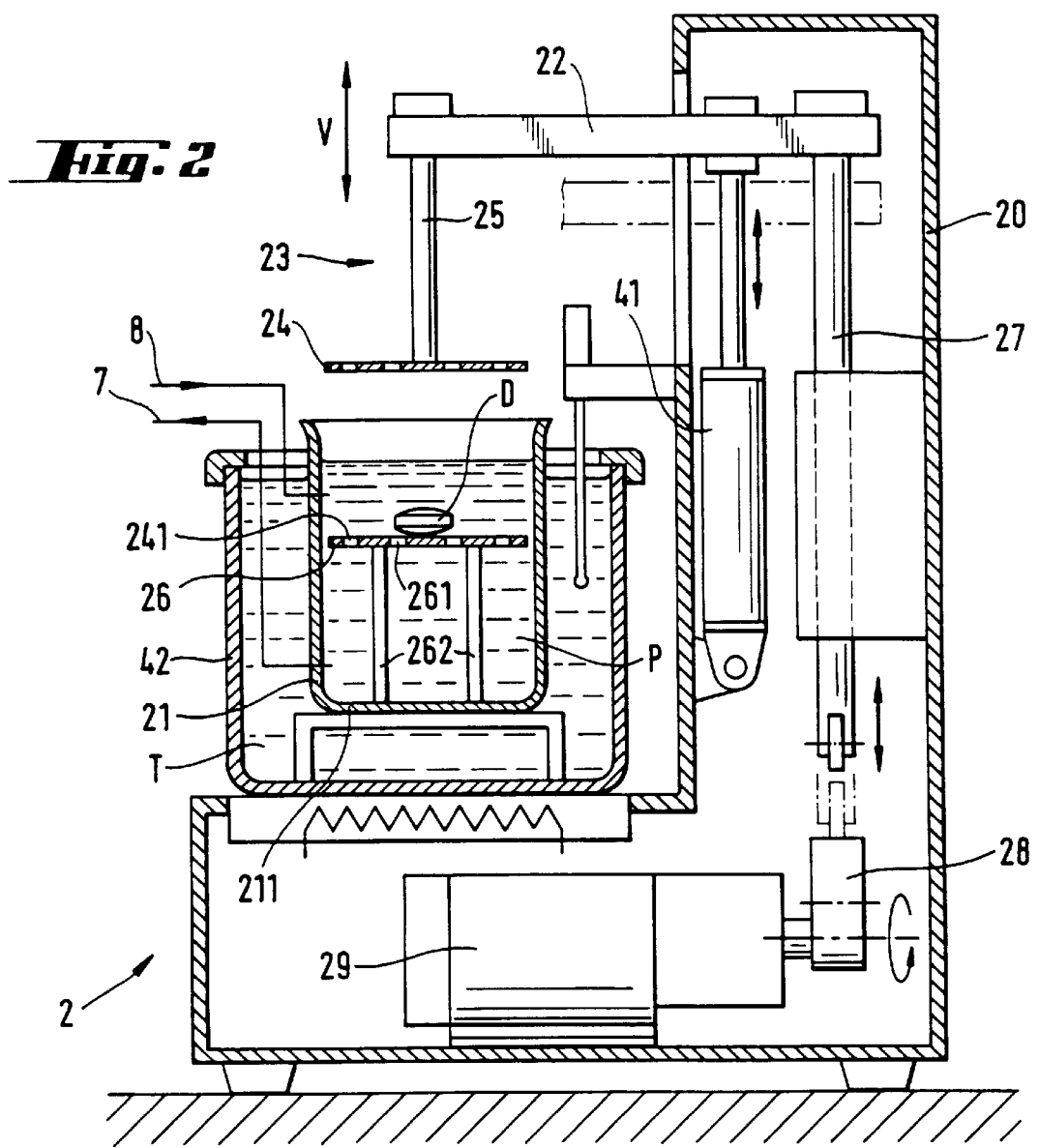

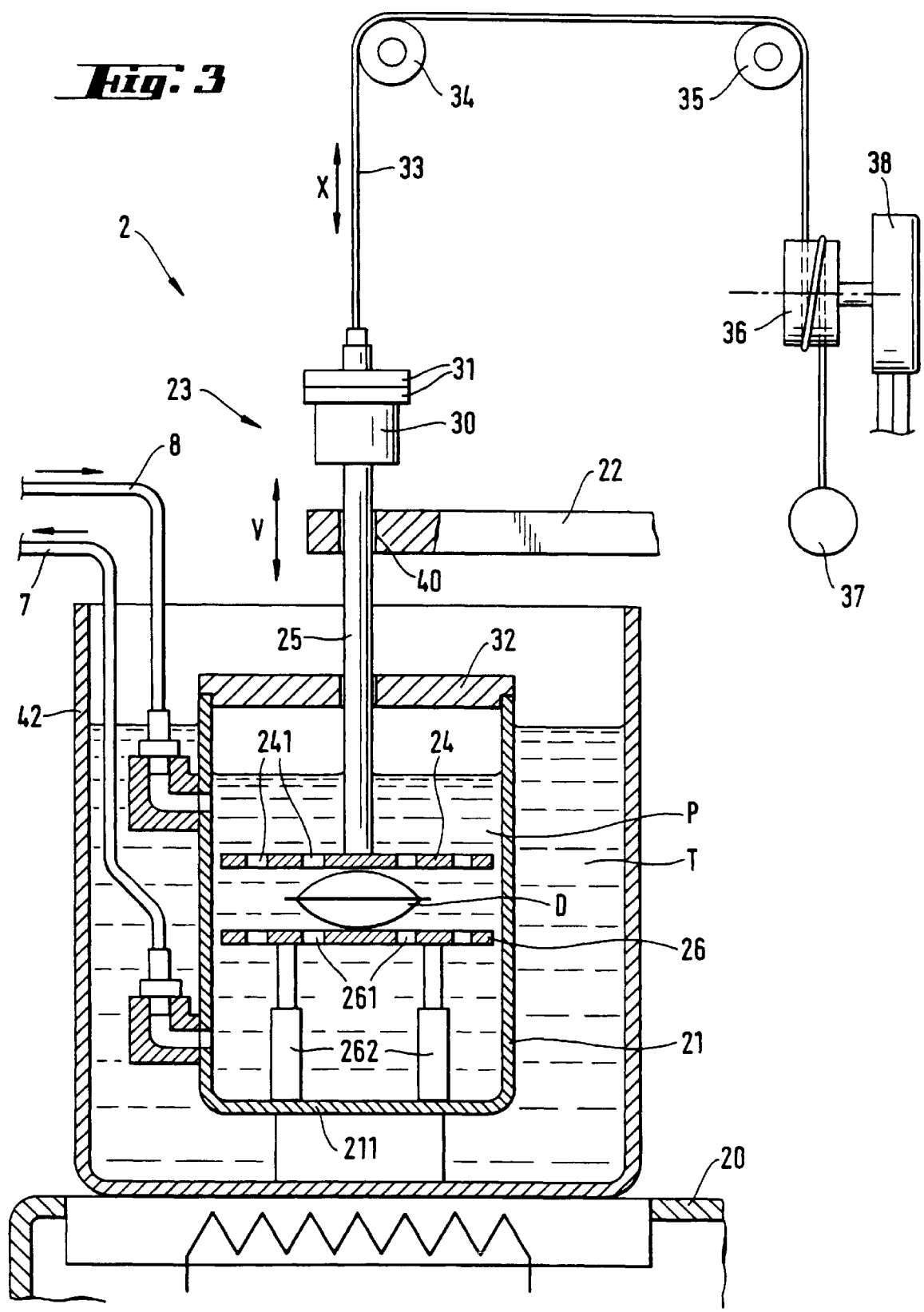

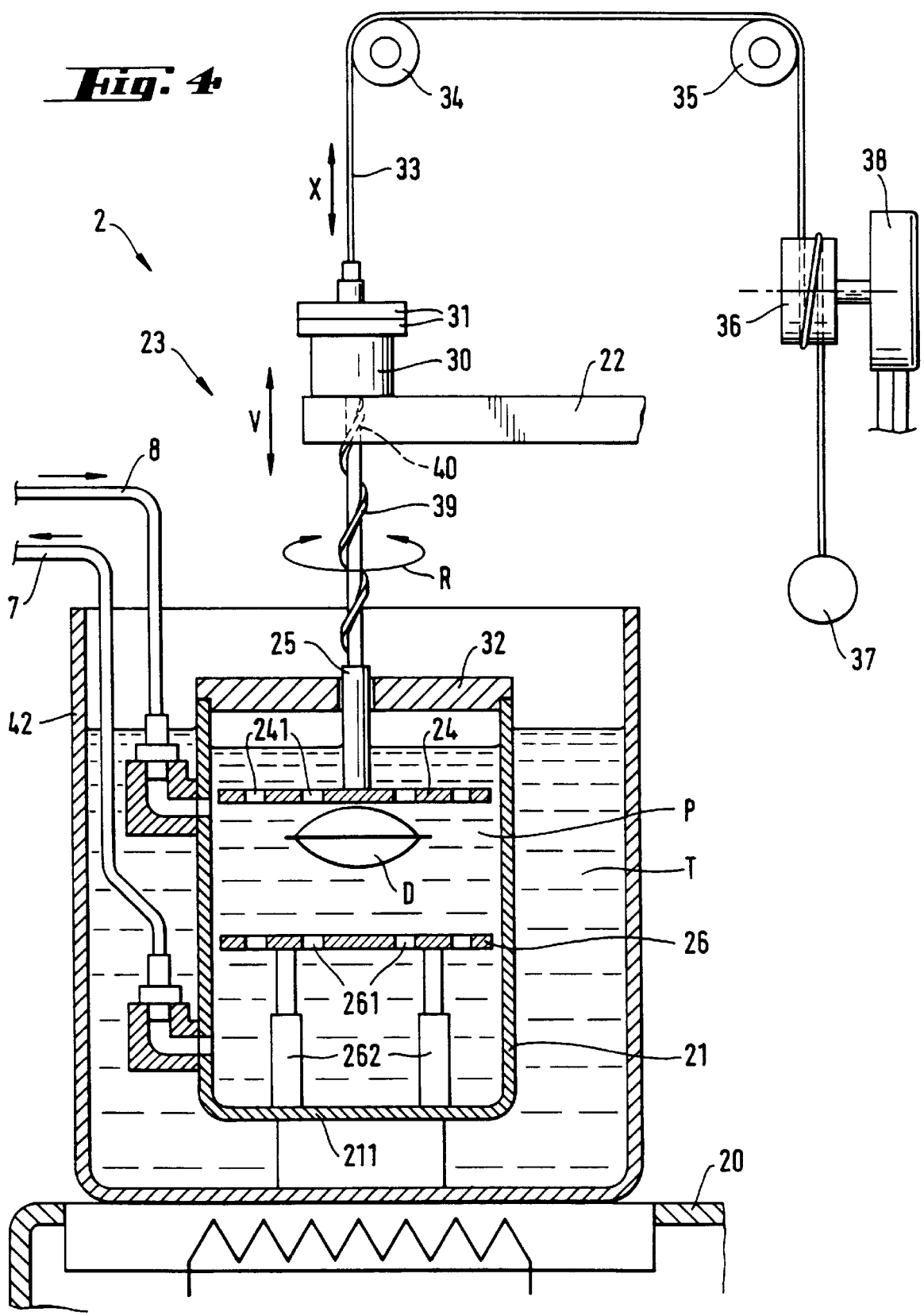

APPARATUS FOR SIMULATING THE EFFECT OF THE LIVING ORGANISM ON THE CHANGE IN SHAPE, THE DISINTEGRATION AND DISSOLUTION BEHAVIOUR AND THE ACTIVE-INGREDIENT RELEASE OF A PHARMACEUTICAL DOSAGE FORM

CROSS-REFERENCE TO RELATED APPLICATIONS

This is a 371 of PCT/EP 94/02485, filed Jul. 28, 1994.

BACKGROUND OF THE INVENTION

The invention relates to an apparatus for simulating the effect of the living organism on the change in shape, the disintegration and dissolution behaviour and the active-ingredient release of a pharmaceutical dosage form according to the preamble of patent claim 1.

Pharmaceutical dosage forms must be adapted to the physiological conditions prevailing on or in the living organism, for example on the skin or in the gastrointestinal tract, in order to be as well suited as possible to the living organism, for example as regards their rate of dissolution and the release of active ingredients. For that purpose, recommended analysis procedures that reproduce as closely as possible the real physiological conditions of the living organism and are intended to allow comparison of the different dosage forms have often been laid down by government bodies. Various analysis apparatuses that take those procedures into account and that are intended to simulate and reproduce the physiological, i.e. including the physico-chemical, conditions of, for example, the gastrointestinal tract are known. For the determination of the disintegration and dissolution behaviour of solid oral dosage forms, for example tablets, dragées and capsules, in the gastrointestinal tract, analysis apparatuses have been developed that, especially, permit analyses in accordance with the "United States Pharmacopoeia XXII, 1990" (USP).

One such analysis apparatus that conforms to the USP (USP XXII, 1990, pages 1577–1583) is based on the wire-basket method proposed in the USP. The test arrangement comprises a cylindrical vessel of transparent material, for example glass or plexiglass, having a hemispherical base. Arranged inside the vessel is a wire basket secured to a shaft rotatable by a motor. The shaft and the wire basket secured thereto are vertically displaceable, so that the distance between the base of the wire basket and the floor of the vessel is adjustable. In order to analyse the disintegration and dissolution behaviour of an oral dosage form, the latter is arranged inside the cage and is lowered together with the cage into the vessel which contains, for example, synthetic gastric or intestinal fluid. The shaft and with it the cage is then rotated by the motor at the speed specified in the test procedure. The rotation of the cage together with the dosage form contained therein is intended to simulate the shearing forces of the fluid acting on the dosage form in the gastrointestinal tract. The gastric or intestinal fluid in the vessel can be pumped round continuously in order to allow the active-ingredient concentration to be determined continuously using an associated analysis unit, for example a spectroscopic analysis unit. In that manner the release of active ingredient by the dosage form in the gastric or intestinal fluid over time can be determined. Because the vessel is transparent, the disintegration of the solid dosage form can be determined visually in accordance with certain predetermined criteria. In particular, the condition of the dosage form is visually assessed periodically over relatively long periods of time.

A further known analysis apparatus is based on the paddle method proposed in the USP (USP XXII, 1990, pages 1577–1583). As in the case of the apparatus described hereinbefore, that analysis apparatus comprises a cylindrical vessel of preferably transparent material and having a hemispherical base. A motor-driven shaft is provided at one end with paddles that are immersed into the gastric or intestinal fluid in the vessel. The shaft is again vertically displaceable to enable the distance between the paddles and the floor of the vessel to be adjusted in accordance with the specifications. In order to be tested, the dosage form is introduced into the fluid. If necessary, the solid dosage form can be weighted with a piece of inert material to prevent it from floating up. The rotation of the paddles agitates the fluid and is intended to simulate the shearing forces of the fluid acting on the dosage form in the gastrointestinal tract. As in the analysis apparatus mentioned hereinbefore, the gastric or intestinal fluid in the vessel can be pumped round continuously in order to allow the active-ingredient concentration to be determined continuously using an associated analysis unit, for example a spectroscopic analysis unit, and thus to establish the active-ingredient-release curve of the dosage form over time or, as already mentioned above, the disintegration of the dosage form can be observed visually.

In an article in the International Journal of Pharmaceutics, 95 (1993), 67–75, 1993, Elsevier Science Publishers B.V., it is proposed that, for improved simulation of the physiological conditions in the gastrointestinal tract, an analysis apparatus based on the paddle method be adapted by adding a number of small polystyrene beads to the gastric or intestinal fluid in the vessel. The polystyrene beads have a diameter of 6.35 mm. In the tests described, up to 4000 beads were added. It is claimed that in the experiments relatively good agreement was found between the results measured and results obtained in animal experiments.

A brochure from SOTAX AG, 4008 Basle, Switzerland, describes a SOTAX tablet-disintegration testing apparatus which allows the disintegration ability of tablets, capsules or dragée cores to be determined in a manner that conforms to the USP. The testing apparatus comprises a number of test tubes of transparent material (glass, plexiglass) which are open at the top and closed off at the bottom by a wire mesh. A number of test tubes are gathered together in a basket frame that is suspended by its central shaft from a gallows-shaped lifting device. The basket frame containing the test tubes is immersed into a cylindrical vessel containing, for example, gastric or intestinal fluid that can be arranged in a temperature-controlled heating bath. The lifting device is connected by a rod to a motor-driven eccentric device arranged inside a housing. By way of the rod the rotation of the eccentric device is converted into a vertical reciprocating movement of the basket frame. In that known apparatus the physiological behaviour of the gastrointestinal tract is simulated by the controlled reciprocating movement of the basket frame containing the test tubes. The immersion of the solid dosage forms lying on the wire mesh closing off the bottom ends of the tubes can be controlled at the same time. It is also possible to vary the immersion frequency, which is customarily fixed. That allows the more or less periodic emergence and floating to the surface of the dosage form that take place in the gastrointestinal tract to be approximated. The test to determine the disintegration behaviour is again carried out, for example, visually in accordance with specific prescribed disintegration criteria that vary according to the dosage form. The dissolution behaviour and the active-ingredient release can again be determined, for example by means of spectroscopy, using a further analysis unit attached to the apparatus.

Although the action of the shearing forces of the test fluid on the dosage form to be tested can be approximated relatively well using those known analysis apparatuses and the results measured also correlate relatively well with, for example, results obtained by means of animal experiments, the known apparatuses nevertheless exhibit a number of disadvantages worthy of improvement. As is known, more or less frequent contractions take place in the gastrointestinal tract. In the stomach, and to a lesser extent also in the intestine, dosage forms are subjected not only to the shearing forces of the fluid but also to pressure and kneading processes by the walls of the stomach and/or of the intestine and/or to pressure waves in the gastric and/or intestinal fluid. Those pressure and kneading processes have a not inconsiderable effect on the rate of dissolution of a dosage form. It is those very pressure and kneading processes, for example in the gastrointestinal tract, that cannot be simulated by the known analysis apparatuses. The attempt to simulate such processes by the addition of a plurality of small beads seems after all rather far removed from the real conditions. The behaviour of novel dosage forms, such as active-ingredient releasing sachets that expand in the body, can be characterised only with difficulty, and even then not completely, using known analysis apparatuses. In particular, it is desirable also to investigate the change in their shape and volume in the gastrointestinal tract. Furthermore, there is a general desire for a test apparatus capable of simulating the effects of pressure and kneading on a pharmaceutical dosage form outside the body, for example on transdermal systems, intrauterine implants or suppositories, ophthalmological implants and inlays, or in veterinary medicine.

The problem underlying the present invention is therefore to mitigate those disadvantages of the analysis apparatuses of the prior art. An analysis apparatus is to be provided which allows both the shearing forces of the fluid and the pressure and kneading effects of the living organism, not solely, but especially, in the gastrointestinal tract, to be simulated. In addition, the analysis apparatus is to provide the preconditions for characterising dosage forms automatically on the basis of their changes in shape and volume.

SUMMARY OF THE INVENTION

All those and other, associated problems are solved by an apparatus for simulating the effect of the living organism on the change in shape, the disintegration and dissolution behaviour and the active-ingredient release of a pharmaceutical dosage form, having the characterising features of patent claim 1. The invention provides especially an apparatus for simulating the effect of the living organism, for example of the gastrointestinal tract, on the change in shape, the disintegration and dissolution behaviour and the active-ingredient release of a pharmaceutical dosage form, which comprises a beaker-shaped container for accommodating a test medium, for example a synthetic gastric or intestinal fluid, and a pharmaceutical dosage form, and an agitating device, suspended from a gallows-shaped boom, for the test medium. The agitating device can be moved periodically into and back out of the beaker, preferably vertically. The vertically reciprocating agitating device comprises a piston-shaped head portion arranged on a piston rod, which head portion is provided with through-openings for the test medium and the distance of which from the container floor can be altered periodically in accordance with the periodic reciprocating movement of the agitating device. Thus by moving the agitating device up and down, on the one hand the flow conditions of the test medium in the gastrointestinal tract can be obtained and, on the other, at the same time the contractions thereof caused by peristalsis and the resulting pressure and kneading effects on the pharmaceutical dosage form can be simulated.

The gallows-shaped boom is preferably connected by way of a rod to a motorised eccentric device, a crank shaft or the like, in such a manner that the rotary movement of the eccentric device can be converted into a periodic vertical reciprocating movement of the gallows-shaped boom. The periodicity of the lifting movement is thus ensured and very easily regulated.

Because the frequency of the vertical reciprocating movement can be regulated and can be adjusted, for example, from zero strokes per minute to as many as 60 strokes per minute, different regions of the gastrointestinal tract can be simulated very well. It is also possible in that manner to reproduce the different activity of the gastrointestinal region at different times of the day, for example during sleeping and waking phases.

In an especially preferred variant of the test apparatus, the test apparatus is equipped with a preferably pneumatic lifting device which allows the gallows-shaped boom to be raised so that, regardless of the particular position of the eccentric device, the agitating device is raised and exerts no pressure on the dosage form. Thus periods of complete rest, for example of the gastrointestinal tract, can be reproduced. It is, of course, also possible to ensure that the agitating device permanently exerts an adjustable pressure on the dosage form in order thus to simulate the permanent pressure of the living organism on the dosage form. The mass of the piston rod and of the head portion is preferably adjustable so that the pressure that the head portion exerts if it comes to rest on the dosage form is from approximately 5 $mN/cm^2$ to approximately 500 $N/cm^2$. The activity of different areas of the gastrointestinal region can thus be simulated even more accurately.

Because an intermediate base provided with through-openings for the test medium is arranged in the container and acts as a support for the dosage form, and because the distance between the intermediate base and the floor of the container is adjustable, the requisite length of stroke, and hence the speed of movement of the agitating device, can be altered.

An especially wide range of potential uses for the apparatus that are especially applicable to the problem of the invention is created by suspending the piston rod connected to the head portion from the gallows-shaped boom in such a manner that it is vertically displaceable relative thereto. In that arrangement, the piston rod preferably passes freely through a bore in the gallows-shaped boom in such a manner that its downward movement is caused by gravity alone and is braked by the gallows-shaped boom. The fact that the piston rod passes freely through the bore allows further downward movement of the gallows-shaped boom if the head portion comes to rest on the dosage form or the beaker floor or the intermediate base. In addition, the piston rod is provided at its end remote from the head portion with an abutment in such a manner that it is carried along during the upward movement of the gallows-shaped boom. If the piston rod is also connected to a length meter that consists, for example, of a thread attached to the back end of the piston rod and connected to a sliding potentiometer, the vertical displacement of the piston rod relative to the gallows-shaped boom can be measured very easily.

In order to characterise the change in shape of a dosage form, it is advantageous if at least the piston-shaped head portion is shaped in such a manner that when it comes to rest on the dosage form it touches the peripheral edges thereof. If the length meter, for example the potentiometer, is connected to a computer unit, the measured lengths of displacement of the piston rod relative to the gallows-shaped boom can be converted into changes in volume, width or thickness of a dosage form disintegrating and/or being dissolved in the test medium. For example, in that manner the increase in volume of an expanding dosage form can be determined very accurately.

Because the piston-shaped head portion can be rotated about the piston rod, which acts as an axle, during its reciprocating movement, the agitation of the fluid can be improved further. It is especially advantageous if the piston rod is provided on its periphery with a thread and the gallows-shaped boom has a threaded bore through which the piston rod passes in such a manner that during the reciprocating movement of the gallows-shaped boom the piston rod rotates until the abutment arranged at the end of the piston rod remote from the head portion rests against the boom.

In order to have the option of keeping the test medium at a desired or prescribed temperature, which as far as possible corresponds to the temperature in the particular part of the body to be simulated, the beaker-shaped container is preferably arranged in a temperature-controlled heating bath.

In order to prevent possible evaporation of the test medium at elevated temperatures, for example at temperatures of from approximately 32° C. to approximately 38° C., the beaker-shaped container is preferably equipped with a removable lid having a through-opening for the piston rod.

For carrying out series tests it is advantageous for several, preferably at least two, agitating devices to be suspended from a gallows-shaped boom, which agitating devices can be moved up and down in a corresponding number of beaker-shaped containers containing the test medium and dosage forms arranged on the intermediate bases. The capacity of the apparatus can be increased further by providing a plurality of gallows-shaped booms having agitating devices suspended from them and a number of beaker-shaped containers corresponding to the number of agitating devices. Such series tests are not limited merely to the disintegration and dissolution behaviour of different dosage forms. It is also possible for chemical and biological processes that play a role therein to be tested at the same time, for example by adding enzymes, salts, acids and the like to the various containers.

The apparatus according to the invention for simulating the physiological conditions is used preferably in an analysis system for determining the disintegration behaviour and/or the dissolution behaviour and the active-ingredient release of pharmaceutical dosage forms. In that system, an analysis unit, for example a spectroscopic analysis unit, is connected to the simulation apparatus for preferably continuous determination of the active-ingredient concentration in a test medium. In that manner it is possible for the change in volume or width and/or thickness of a dosage form to be determined continuously and for the release of active-ingredient, the energy absorption and the progress of chemical or biological processes to be detected in parallel therewith. The analysis system according to the invention can be used to test and to characterise tablets, dragées, capsules, transdermal systems, intrauterine inlays, suppositories, ophthalmological inlays or implants, or devices for use in veterinary medicine.

BRIEF DESCRIPTION OF THE DRAWINGS

The invention is explained in detail below with reference to several variants with all their associated details that are essential to the invention and with reference to the diagrammatic drawings. In the drawings, the same components are given the same reference numerals in each case.

FIG. 1 is a basic block diagram of an analysis system for determining the change in shape, the disintegration and dissolution behaviour and the active-ingredient release of a pharmaceutical dosage form, FIG. 2 shows a test apparatus according to the invention, and FIGS. 3 and 4 show two variants of the test apparatus according to the invention with the agitating device in two different positions.

DESCRIPTION OF THE PREFERRED EMBODIMENTS

FIG. 1 is a block diagram of an analysis system for testing the disintegration and dissolution behaviour and/or the active-ingredient release of a preferably solid pharmaceutical dosage form. It has been used in the past above all to test dosage forms, such as tablets or dragées. Owing to the design of the test apparatuses, those tests had to be limited essentially to the effect of the shearing forces of a body fluid in which the dosage form was arranged. The analysis apparatus as a whole has the reference numeral 1 in FIG. 1. It comprises a test apparatus 2 for the pharmaceutical dosage form and an analysis device 4, for example a spectrometer, connected thereto. A pump device 3 pumps a test medium, for example a body fluid such as gastric or intestinal fluid, from the test device 2 via a line 7 to the analysis unit 4. From there, the test medium returns via a line 8 to the test apparatus 2. The test apparatus 2 and the analysis device 4 are connected via digital 9 and analog 10 data and/or control lines to a computer unit 6. An analog amplifier 5 is used to amplify the analog signals. Using the computer unit 6, control commands can be passed on to the attached devices and the measured data can be evaluated.

The substantial innovation of an analysis system of that type that also allows other types of dosage form, for example expanding dosage forms, transdermal systems, intrauterine inlays or suppositories, ophthalmological implants and inlays, or devices for use in veterinary medicine to be characterised, or the effect of the living organism on those dosage forms to be tested, consists in the development according to the invention of the test apparatus 2.

FIG. 2 shows a first embodiment of a test apparatus 2 according to the invention. It has a beaker-shaped container 21 for accommodating a test medium P, for example a synthetic gastric or intestinal fluid, and a pharmaceutical dosage form D, and an agitating device 23, suspended from a gallows-shaped boom 22, for the test medium P. The agitating device 23 can be moved into and back out of the beaker 21 periodically, preferably vertically, as indicated by the double arrow V. The vertically reciprocating agitating device 23 comprises a piston-shaped head portion 24 arranged on a piston rod 25 and provided with through-openings 241 (FIG. 3) for the test medium P; the distance of the head portion from the container floor 211 (FIG. 3) can be altered periodically in accordance with the periodic reciprocating movement of the agitating device 23. In that manner, by reciprocating the agitating device 23, it is possible on the one hand to influence the flow conditions of the test medium P and, for example, reproduce those of the gastrointestinal tract and on the other hand to simulate pressure and kneading influences on the dosage form D at the same time. In that manner, for example, the contractions of the gastrointestinal tract caused by peristalsis can be reproduced.

The simulation possibilities are not, however, limited to the gastrointestinal tract alone. The fact that the dosage form D can be subjected to pressure and kneading action by the agitating device 23 means that the effect of other parts of the body, for example on suppositories, intrauterine inlays or on ophthalmological implants or inlays can also be tested. It is also possible, for example, to track the release of active ingredient by a transdermal system under pressure and kneading influences.

As shown in the drawing, the gallows-shaped boom 22 is connected via a rod 27 to an eccentric device 28, a crank shaft or the like which is driven by an electric motor 29. In that manner the rotary movement of the eccentric device 28 is converted into a periodic vertical reciprocating movement V of the gallows-shaped boom 22, and hence of the agitating device 23. In that manner the periodicity of the lifting movement is ensured, and the stroke frequency and the speed of the lifting movement can be very well controlled. Part of the boom 22, the rod 27, the eccentric device 28 and the drive motor 29, as well as other control and regulating devices that may be necessary, are preferably accommodated in a housing 20.

The frequency of the vertical reciprocating movement V can preferably be regulated and is preferably adjustable, for example, from zero strokes per minute to as many as 60 strokes per minute. In that manner, for example, different regions of the gastrointestinal tract or other regions of the living organism can be simulated individually. This also allows the different activity of the living organism at different times of the day, for example during sleeping and waking phases, to be taken into account.

It is especially advantageous for the test apparatus 2, as shown in FIG. 2, to be equipped with a preferably pneumatic lifting device 41 that allows the gallows-shaped boom 22 to be raised. The agitating device 23 can thus be raised regardless of the particular position of the eccentric device 28, with the result that the head portion 24 does not exert any pressure on the dosage form D. That enables periods of complete rest, for example of the gastrointestinal tract, to be reproduced. Of course the pneumatic lifting device 41 can also be constructed in such a manner that the agitating device 23 can be pushed down in order thus to exert a permanent, preferably adjustable, pressure on the dosage form D. It is thus possible to simulate the exertion of permanent pressure of a specific magnitude by the living organism on the dosage form D.

In order to have the option of keeping the test medium P at a desired or prescribed temperature that corresponds as far as possible to the temperature in the particular part of the body to be simulated, the beaker-shaped container 21 is arranged in an outer container 42 (FIG. 3) having a temperature-controlled heating bath T (FIG. 3). For that purpose that part of the housing 20 that serves as the surface on which the temperature-controlled container 42 stands can have a heating plate connected to a temperature-control device that monitors the temperature of the heating bath T and controls the heat output of the heating plate as required.

FIGS. 3 and 4 show two variants of the test apparatus 2 according to the invention that allow an especially wide range of possible uses. In those variants the piston rod 25 connected to the head portion 24 is suspended from the gallows-shaped boom 22 in such a manner that it is vertically displaceable relative thereto, as shown by the double arrow X. In that arrangement, the piston rod 25 preferably passes freely through a bore 40 in the gallows-shaped boom 22 in such a manner that its downward movement is caused by gravity alone and is braked by the gallows-shaped boom 22. The fact that the piston rod 25 passes freely through the bore 40 allows further downward movement of the gallows-shaped boom 22 if the head portion 24 comes to rest on the dosage form D, which in the case illustrated is an expanding, active-ingredient releasing sachet, or on the beaker floor 211. At its end remote from the head portion 24, the piston rod 25 is provided with an abutment 30 in such a manner that it is carried along during the upward movement of the gallows-shaped boom 22.

According to the drawings, the piston rod 25 is connected to a length meter which consists, for example, of a cord 33 attached to the back end of the piston rod 25 and connected via deflecting rollers 34, 35 to a rotary or sliding potentiometer 38 having a cord drum 36. A counter-weight 37 serves to tension the cord 33. In that manner the vertical displacement X of the piston rod 25 relative to the gallows-shaped boom 22 can be measured by way of the potentiometer 38. The change in shape of the dosage form D in question can be deduced from the vertical displacement of the piston rod 25.

As shown in FIGS. 3 and 4, the beaker 21 is preferably equipped with an intermediate base 26 which is provided with through-openings 261 for the test medium P. The intermediate base is, for example, a type of sieve plate made from glass or plexiglass. The height of the intermediate base 26 from the beaker floor 211 is preferably adjustable. For that purpose, for example, it is supported on telescopically extensible feet 262. The dosage form D in that case lies on the intermediate base 26 and/or can be clamped between that base and the head portion 24. In that manner the requisite length of stroke, and hence the speed of the agitating device 23, can be altered very easily.

The mass of the piston rod 25 and of the head portion 24 are preferably adjustable in such a manner that the pressure that the head portion 24 exerts if it comes to rest on the dosage form D is from approximately 5 $mN/cm^2$ to approximately 500 $N/cm^2$. For example, for that purpose small plates 31 of different weights can simply be arranged on the piston rod 25 in the region of the abutment 30. That enables the activity of different regions of the living organism, for example in the gastrointestinal region, to be simulated even more accurately.

In order to characterise the change in shape of a dosage form D, it is advantageous for at least the piston-shaped head portion 24 to be shaped in such a manner that when it comes to rest on the dosage form D it touches the peripheral edges thereof. The head portion 24 is, for example, approximately hemispherical or conical in shape. The shape of the intermediate base can also be made approximately to complement the shape of the head portion when its shape is other than a plane plate. When the head portion 24 comes to rest on the dosage form D, the piston rod 25 is displaced relative to the gallows-shaped boom 22. The length of displacement is detected by the length meter. The measured lengths of displacement of the piston rod 25 relative to the gallows-shaped boom 22 are converted by the computer unit 6 into changes in the volume, width or thickness of the dosage form changing shape, expanding, disintegrating and/or being dissolved in the test medium. In that manner, for example, the increase in volume of an expanding dosage form can be determined very accurately.

In the variant of the test apparatus shown in FIG. 4, the piston rod 25 is provided, at least at its end remote from the head portion 24, with an external thread 39. The bore 40 in the gallows-shaped boom 22 is likewise provided with a corresponding thread. As a result, the piston rod 25, which passes through the bore 40, is rotated (arrow R) during the reciprocating movement of the gallows-shaped boom 22 until the abutment 30 arranged at the end of the piston rod 25 remote from the head portion 24 is resting on the boom 22. Because the piston-shaped head portion 24 can be rotated about the piston rod 25, which acts as an axle, during its reciprocating movement, the agitation of the test medium P can be improved further.

In order to prevent possible evaporation of the test medium P at elevated temperatures, for example at temperatures from approximately 32° C. to 38° C., the beaker-shaped container 21 is preferably equipped with a removable lid 32 which has a through-opening for the piston rod 25.

For carrying out series tests it is advantageous for several, preferably at least two, agitating devices 23 to be suspended from a gallows-shaped boom 22, the agitating devices being movable in a reciprocating manner in a corresponding number of beaker-shaped containers 21 containing the test medium P and dosage forms D arranged on the beaker floors 211 or on the intermediate bases 26. The capacity of the apparatus 2 can be increased further by providing a plurality of gallows-shaped booms 22 having agitating devices 23 suspended from them and a number of beaker-shaped containers 21 corresponding to the number of agitating devices 23. Such series tests are not limited merely to the changes in shape or the disintegration and dissolution behaviour of different dosage forms D. It is also possible for chemical and biological processes that play a role therein to be tested, for example by adding enzymes, salts, acids and the like to the various containers.

The apparatus 2 according to the invention for simulating the physiological conditions is used preferably in an analysis system for determining the change in shape, the disintegration behaviour and/or the dissolution behaviour and the active-ingredient release of pharmaceutical dosage forms. In that system, an analysis unit 4, for example a spectroscopic analysis unit, is connected to the simulation apparatus 2 for preferably continuous determination of the active-ingredient concentration in a test medium. In that manner it is possible for the change in volume or width and/or thickness of a dosage form to be determined continuously, and for the release of active-ingredient, the energy absorption and the progress of chemical or biological processes to be detected in parallel therewith. The analysis system according to the invention can be used to test and to characterise tablets, dragées, capsules, transdermal systems, intrauterine inlays, suppositories, ophthalmological inlays or implants, or devices for use in veterinary medicine.

What is claimed is:

1. An apparatus for simulating the effect of a living organism on the change in shape, the disintegration and dissolution behaviour and the active-ingredient release of a pharmaceutical dosage form, comprising a beaker-shaped container for accommodating a test medium and the pharmaceutical dosage form and an agitating device for agitating the test medium, which agitating device can be moved periodically in a reciprocating movement into and back out of the container, wherein the agitating device comprises a piston-shaped head portion arranged on a piston rod, which head portion is provided with through-openings for the test medium and the distance of the piston-shaped head portion from the container floor can be altered periodically in accordance with the periodic reciprocating movement of the agitating device, wherein, in a first alternative, the piston rod is suspended from a gallows-shaped boom or, in a second alternative, the piston rod passes through a bore in the gallows-shaped boom in such a manner that downward movement of the piston-shaped head portion arranged on the piston rod is caused by gravity alone and wherein there is arranged in the container an intermediate base supported on the container floor, the base being provided with through-openings for the test medium and serving as a support for the dosage form, wherein the distance between the intermediate base and the container floor is adjustable by a means for adjusting the distance between the base and the floor.

2. The apparatus according to claim 1, wherein the gallows-shaped boom is connected by way of a rod to an eccentric device wherein the rotary movement of the eccentric device can be converted into the periodic vertical reciprocating movement of the gallows-shaped boom.

3. The apparatus according to claim 2, wherein the frequency of the periodic vertical reciprocating movement can be regulated and can be adjusted from zero strokes per minute up to about 60 strokes per minute.

4. The apparatus according to the second alternative of claim 1, wherein the piston rod connected to the head portion is suspended from the gallows-shaped boom in such a manner that the head portion is vertically displaceable relative to the gallows-shaped boom.

5. The apparatus according to the second alternative of claim 1, wherein a downward movement of the piston-shaped head portion arranged on the piston rod is braked by the gallows-shaped boom, and whenever the head portion comes to rest on the dosage form or on the container floor, the bore in the gallows-shaped boom allows further downward movement of the piston-rod, the piston rod being provided, at the end of the piston rod remote from the head portion, with an abutment in such a manner that the piston-shaped head portion arranged on the piston rod is carried along during the upward movement of the gallows-shaped boom.

6. The apparatus according to claim 2, further comprising a pneumatic lifting device which allows the gallows-shaped boom to be raised regardless of the position of the eccentric device such that the head portion can be raised and brought reliably out of contact with the dosage form.

7. The apparatus according to claim 1, wherein the mass of the piston rod and of the head portion can be altered in such a manner that the pressure exerted by the head portion, whenever the head portion comes to rest on the dosage form, is from approximately 5 $mN/cm^2$ to approximately 500 $N/cm^2$.

8. The apparatus according to claim 1 wherein the agitating device is capable of moving vertically.

9. The apparatus according to claim 5, wherein the piston rod is connected to a length meter by means of which the vertical displacement of the piston rod relative to the gallows-shaped boom can be determined.

10. The apparatus according to claim 1, wherein at least the piston-shaped head portion is shaped in such a manner that whenever the head portion comes to rest on the dosage form, the head portion touches a peripheral edge of the pharmaceutical dosage form.

11. The apparatus according to claim 9, wherein the length meter is connected to a computer unit by means of which the measured displacement of the piston rod relative to the gallows-shaped boom can be converted into changes in volume, width or thickness of the pharmaceutical dosage form expanding, disintegrating or being dissolved in a test medium.

12. The apparatus according to claim 5, wherein the piston-shaped head portion can be rotated about the piston rod, which acts as an axle, during the reciprocating movement of the piston-shaped head portion arranged on the piston rod.

13. The apparatus according to claim 12, wherein the piston rod is provided on the periphery of the piston rod with a thread and the gallows-shaped boom has a threaded bore through which the piston rod passes in such a manner that during the reciprocating movement of the gallows-shaped boom the piston rod rotates until the abutment arranged at the end of the piston rod remote from the head portion is resting on the boom.

14. The apparatus according to claim 1, wherein the beaker-shaped container is arranged in a temperature-controlled heating bath.

15. The apparatus according to claim 1, wherein the beaker-shaped container is equipped with a removable lid which has a through-opening for the piston rod.

16. The apparatus according to claim 8, wherein the apparatus comprises at least two of said agitating devices that can be moved up and down in a corresponding number of beaker-shaped containers.

17. The apparatus according to claim 16, wherein the apparatus comprises a plurality of gallows-shaped booms.

18. The analysis system for determining the change in shape, the disintegration behaviour or the dissolution behaviour and the active-ingredient release of pharmaceutical dosage forms, comprising an analysis apparatus for simulating the effect of the living organism, and an associated analysis unit, for continuous determination of the active-ingredient concentration in a test medium, wherein the analysis apparatus is an apparatus according to claim 1.

19. The analysis system according to claim 18, wherein the pharmaceutical dosage is in the form of a tablet, a dragée, a capsule, a transdermal system, an intrauterine inlay, a suppository, an ophthalmological inlay or implant, or a device for use in veterinary medicine.

20. The apparatus according to claim 1 wherein the test medium is a synthetic gastric or intestinal fluid.

21. The apparatus according to claim 1 wherein the piston rod is suspended from the gallows-shaped boom.

22. The apparatus according to claim 1, wherein the piston-shaped head portion can be rotated about the piston rod, which acts as an axle, during the reciprocating movement of the piston-shaped head portion arranged on the piston rod.

23. The apparatus according to claim 2 wherein the eccentric device is motor driven.

* * * * *

UNITED STATES PATENT AND TRADEMARK OFFICE
CERTIFICATE OF CORRECTION

PATENT NO. : 5,827,984
DATED : OCTOBER 27, 1998
INVENTOR(S) : JOEL SINNREICH ET AL.

It is certified that error appears in the above-identified patent and that said Letters Patent is hereby corrected as shown below:

Title page, Item [87], should read:

-- [87] PCT Pub. No.: WO 95/04923

PCT Pub. Date: February 16, 1995 --.

Signed and Sealed this

Twenty-seventh Day of July, 1999

Attest:

Q. TODD DICKINSON

*Attesting Officer*   Acting Commissioner of Patents and Trademarks